(12) United States Patent
Paakinaho et al.

(10) Patent No.: US 9,777,148 B2
(45) Date of Patent: Oct. 3, 2017

(54) BIOCOMPATIBLE MATERIAL AND DEVICE

(75) Inventors: Kaarlo Paakinaho, Tampere (FI); Harri Heino, Tampere (FI); Pertti Törmälä, Tampere (FI)

(73) Assignee: BIORETEC OY, Tampere (FI)

( * ) Notice: Subject to any disclaimer, the term of this patent is extended or adjusted under 35 U.S.C. 154(b) by 621 days.

(21) Appl. No.: 13/697,574

(22) PCT Filed: May 11, 2010

(86) PCT No.: PCT/FI2010/050384
§ 371 (c)(1),
(2), (4) Date: Apr. 30, 2013

(87) PCT Pub. No.: WO2011/141615
PCT Pub. Date: Nov. 17, 2011

(65) Prior Publication Data
US 2013/0211000 A1    Aug. 15, 2013

(51) Int. Cl.
| | | |
|---|---|---|
| A61L 27/46 | (2006.01) | |
| C08L 67/00 | (2006.01) | |
| A61L 27/50 | (2006.01) | |
| A61L 27/58 | (2006.01) | |
| C08L 67/04 | (2006.01) | |

(52) U.S. Cl.
CPC .............. *C08L 67/00* (2013.01); *A61L 27/46* (2013.01); *A61L 27/50* (2013.01); *A61L 27/58* (2013.01); *C08L 67/04* (2013.01)

(58) Field of Classification Search
CPC ..................................................... A61L 27/46
See application file for complete search history.

(56) References Cited

U.S. PATENT DOCUMENTS 4,898,186 A * 2/1990 Ikada et al. ..................... 606/62
4,968,317 A 11/1990 Törmälä et al.
5,981,619 A * 11/1999 Shikinami ............... A61L 27/46
   264/320
6,228,111 B1 5/2001 Törmälä et al.
(Continued)

FOREIGN PATENT DOCUMENTS

CN 101528772 A 8/2009
DE 112006000778 T5 2/2008
(Continued)

OTHER PUBLICATIONS

PCT/ISA/210—International Search Report—Feb. 9, 2011 (Issued in PCT/FI2010/050384).
(Continued)

*Primary Examiner* — Michael Pepitone
(74) *Attorney, Agent, or Firm* — Berggren, Inc.

(57) ABSTRACT

A biodegradable composite material or device including at least one biodegradable polymer matrix material and at least one filler component. The material or device has an initial shape and at least one evolved shape. The evolved shape is different from the initial shape. The initial shape is adapted to change towards the evolved shape. The filler component is adapted to accelerate and/or amplify the transformation from the initial shape towards the evolved shape when the external stimulus for transformation is given by physiological conditions. Also a method to control the shape transformation rate of a composite material or device.

4 Claims, 5 Drawing Sheets

(56) References Cited

U.S. PATENT DOCUMENTS

| | | |
|---|---|---|
| 6,281,261 B1 | 8/2001 | Bennington |
| 8,652,621 B2 | 2/2014 | Weigel et al. |
| 2008/0234730 A1 | 9/2008 | Cotton et al. |
| 2009/0149856 A1* | 6/2009 | Paakinaho ............ A61B 17/866 606/60 |

FOREIGN PATENT DOCUMENTS

| | | |
|---|---|---|
| EP | 1056487 B1 | 5/2004 |
| WO | WO-2008/129245 A1 | 10/2008 |
| WO | WO-2010/049521 A1 | 5/2010 |

OTHER PUBLICATIONS

X Zheng et al., "Shape memory properties of poly(D,L-lactide)/hydroxyapatite composites"; Biomedicals; vol. 27, No. 24, 2006, pp. 4288-4295.
T Ohki et al; Mechanical and shape memory behavior of composites with shape memory polymer; Composites Part A 35, 2004; pp. 1065-1073.
X Zheng et al.; Effect of In Vitro Degradation of Poly(D,L-lactide)/β-tricalcium Composite on Its Shape-Memory Properties; Journal of Biomedical Materials Research Part B; Applied Biomaterials, vol. 86 No. 1, 2008, pp. 170-180.
A Lendlein et al.; Biodegradable, Elastic Shape-Memory Polymers for Potential Biomedical Applications; Science 1673, 2002.
Supplementary European Search Report—May 12, 2014 (Issued in Counterpart Application No. 10851324.3).
K. Gall et al.; "Shape memory polymer nano-composites", Acta Materialia Inc., Published by Elsevier Science Ltd; vol. 50, Jan. 1, 2002 ; pp. 5115-5126.

* cited by examiner

BIOCOMPATIBLE MATERIAL AND DEVICE

CROSS-REFERENCE TO RELATED APPLICATIONS

This application is the national phase under 35 U.S.C. §371 of PCT/FI2010/050384 filed 11 May 2010.

FIELD OF THE INVENTION

The present invention relates to biocompatible, biodegradable materials and devices, especially to composite materials and devices that are fabricated of biodegradable polymers, copolymers or polymer blends and that contain filler component. The invention also relates to a method to control shape transformation of biodegradable polymer composite material or device in physiological conditions.

BACKGROUND

Shape-memory effect has been described for different material classes: polymers, metals and ceramics. First materials with shape-memory were metallic alloys. Shape-memory materials are stimuli-responsive materials and are used in different fields of industry, e.g in aircraft, piping, textiles, packaging, optometry and in medicine e.g. in orthopedics and minimally invasive surgery. Over shape-memory metallic alloys and ceramics, shape memory polymers have, for example, the advantage of light weight, low cost, good processability, high shape deformability and shape recoverability.

Shape-memory polymers are a class of smart and functional polymers. Shape-memory polymeric material may be biodegradable or non-biodegradable. Combination of shape-memory capability, biocompatibility, biodegradability and tailored mechanical properties can be mentioned to highlight the versatility of shape-memory polymers as biomaterials and their applicability in medical devices.

Shape-memory is a material property where the deformed polymeric material has an ability to return from a deformed, temporary shape, towards the original, permanent shape. Shape-memory polymers and products made of them can change their shapes from a temporary shape to their original shapes under appropriate activation or external stimulus such as e.g. temperature, light, pH, solvent composition, specific ions or enzymes. A change in shape induced by a change in temperature is called thermally induced shape memory effect.

Conventional shape-memory effect results from the polymer's structure like a multiblock copolymer structure. Shape memory polymers generally contain two separate phases (like different components on molecular level): a fixing phase and a reversible phase. Fixing phase may contain physical or chemical cross-linking molecular structure (cross-linked polymer network) or crystalline phase and reversible phase may be amorphous.

Shape-memory polymers have potential applications also in medical devices. If the medical device is not intended to be permanent it is possible to use biodegradable polymer(s). Promising fields are minimally invasive surgery and also scaffolding and suturing devices for assisting in tissue repair. Following publications describe the aforementioned and other applications and devices, e.g. Lendlein and Langer, Science 296 (2002) 1673-6, U.S. Pat. No. 6,281,261, EPO Pat no. 1,056,487.

One limit of prior art biodegradable shape-memory polymers is that shape-memory effect is typically thermally induced, which usually means temperatures above polymer glass transition temperature, $T_g$, typically temperatures between 45° to 70° C. Another disadvantage of prior art shape-memory polymers, is their low mechanical strength.

In order to improve the material properties or obtain new functions of shape-memory polymers, shape-memory composites and blends can be prepared, as described in Zheng et al., Biomaterials 27 (2006) 4288-4295, Ohki et al., Composites: Part A 35 (2004) 1065-1073. However the shape memory effect of these composites is also thermally induced, which may restrict their use in medical applications.

Biodegradable medical devices, which have shape-memory effect induced by physiological conditions at temperature of 37° C., are described in U.S Patent application 20090149856.

Some objects of the present invention are to produce composites or devices with an adequate mechanical properties and whose shape transformation at physiological conditions can be controlled to obtain rapid and increased degree of the shape transformation. This may improve e.g. an initial and short term self-locking and fixation strength of the medical devices.

SUMMARY

The present invention provides a method to control the speed and degree of the change of the shape of a deformed biodegradable polymer composite material or device for surgical applications, and a material or device which has in physiological conditions, without additional external stimulus, an ability to undergo a controlled dimensional change with a controlled rate and extent, being at the same time able to exert forces on the healing tissues for a certain time. Controlled dimensional change may be substantially immediate after exposure of the composite material or device in physiological conditions.

According to a first aspect of the present invention there is provided a biodegradable composite material or a device which include at least one biodegradable polymer matrix material and at least one filler component. A composite material or device has an initial shape and at least one evolved shape. The evolved shape is different from the initial shape and the initial shape is adapted to change towards the evolved shape. Evolved shape is recovered under external stimulus given by physiological conditions. In the present invention filler blending advantageously accelerates and/or amplifies the transformation from the initial shape towards the evolved shape in the physiological conditions.

According to an embodiment of the invention a filler component may be hydrophilic enhancing water absorption. Due to the hydrophilic nature of a filler a water uptake of the composite may also be increased. Filler component may also have buffering capacity which will neutralize the acidic degradation products thus further enhancing the material biocompatibility. Filler component may also enhance visibility for example during surgical operation or imagining.

According to an advantageous embodiment of the invention, polymer matrix consists of biodegradable polymer, copolymer and/or polymer alloy matrix.

According to an advantageous embodiment of the invention, the initial shape is programmed to adapt towards a predetermined tension level and the device is capable of restoring this predetermined tension level by stress generation or relaxation.

According to an embodiment of the invention, the amount of filler component is 0.5-50 or more weight-%, preferably 5-15 weight-% and most preferably 5-10 weight-%.

According to a further aspect of the invention there is provided a method to control the speed and degree of the change of the shape of a biodegradable polymer composite material or device. The method comprises: selecting a biodegradable polymer matrix material, selecting a filler component, selecting the relative amount of the filler component in the mixture of the biodegradable polymer matrix material and the filler component, mixing the biodegradable polymer matrix material and the filler component in said relative amount by conventional melt processing to form a composite and programming of an initial shape in a deformation process of the said composite.

According to an embodiment of the invention, the deformation process comprises orientation of the composite using predetermined draw ratio between 1.5-10, preferably between 3-5.

DESCRIPTION OF THE DRAWINGS

In the following, the invention will be discussed with reference to accompanying figures, where.

DETAILED DESCRIPTION OF EXAMPLE EMBODIMENTS

Figure 1:
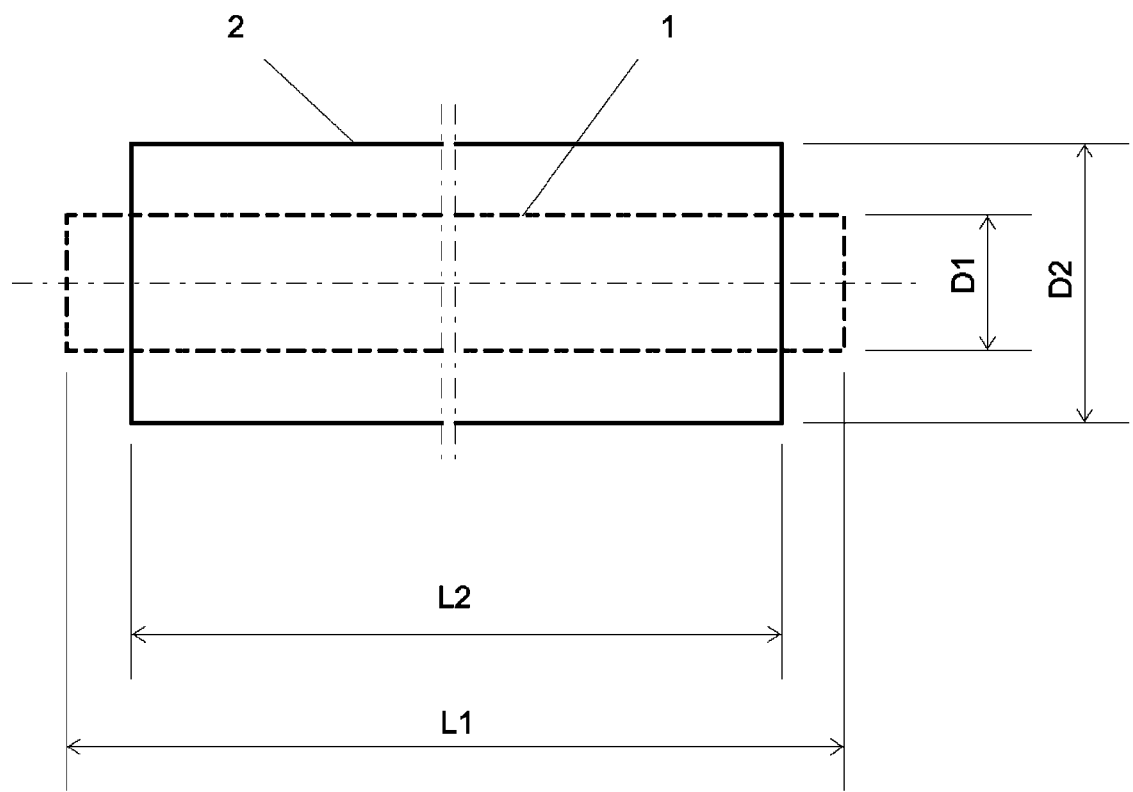
FIG. 1 shows a schematic figure of a change of a shape of a composite material or device having a shape transformation capability.

The present invention describes the ability of a composite material or device to change from initial shape towards the evolved shape (which is referred also as shape transformation or shape-memory effect herein after) in certain controlled and predetermined speed and to provide a predetermined stress and/or strain in tissue conditions which further generate substantially immediate self-locking and auto-compression of the device, such as nails, on the healing tissues, for example in the fracture fixation. In the present invention the combination of shape-memory effect (shape transformation) and stress generation and relaxation is designated as mechanically active shape-memory.

The present invention relates to a biocompatible, at least partially biodegradable composite material or medical device which is made of at least one biodegradable matrix material, which biodegradable matrix may be a synthetic or natural based or fully or partially degradable. At least one biodegradable matrix material may be selected from among polymers like homopolymers or copolymers. A polymeric matrix material may be an alloy of two or more polymers. In this application polymer alloy is referred also as a polymer blend. Biodegradable matrix material may also have a composition and/or structure which has shape-memory capability or potential to be programmed to have shape-memory.

The biodegradable polymeric materials may be selected, for example, from among the following materials: polyglycolide (PGA), copolymers of glycolide, polylactides, copolymers of polylactide, unsymmetrically 3,6-substituted poly-1,4-dioxane-2,5 diones, poly-β-hydroxybutyrate (PHBA), PHBA/β-hydroxyvalerate copolymers (PHBA/HVA), poly-β-hydroxypropionate (PHPA), poly-p-dioxanone (PDS), poly-δ-valerolactone, poly-ε-caprolactone, methylmethacrylate-N-vinyl pyrrolidine copolymers, polyesteramides, polyesters of oxalic acid, polydihydropyrans, polyalkyl-2-cyanoacrylates, polyurethanes (PU), polyvinylalcohol (PVA), polypeptides, poly-β-malic acid (PMLA), poly-β-alkanoic acids, polyethyleneoxide (PEO) and chitine polymers. Copolymers of glycolide comprise, for example, glycolide/L-lactide copolymers (PGA/PLLA) and glycolide/trimethylene carbonate copolymers (PGA/TMC). Polylactides comprise, for example, poly-L-lactide (PLLA), poly-D-lactide (PDLA) and poly-DL-lactide (PDLLA). Copolymers of polylactide comprise, for example, L-lactide/DL-lactide copolymers, L-lactide/D-lactide copolymers, lactide/tetramethylglycolide copolymers, lactide/trimethylene carbonate copolymers, lactide/δ-valerolactone copolymer, lactide/c caprolactone copolymer, polydepsipeptides (glycine-DL-lactide copolymer), polylactide/polyethylene oxide copolymers, glycolide/L-lactide (PGA/PLLA)/polyethylene glycol (PEG) copolymers and polylactide/polyethylene glycol (PEG) copolymers.

According to an advantageous embodiment of the invention a biocompatible, biodegradable composite material or medical device consist of at least one polymeric matrix component, and at least one distinct constituent material or phase, on a scale larger than atomic. The matrix of a composite is preferably polymeric. Polymeric matrix enables the formation of oriented chain structure during orientation programming which further enables the mechanically active shape-memory behaviour of the composite material or device in the physiological conditions. Physiological condition means in this context an aqueous environment and temperature at the range of 35° C. to 42° C. In vitro studies are performed to simulate the physiological conditions.

A constituent phase may be a filler component, which may be at least one of the following: an organic material, a inorganic material, a synthetic material, a natural based material or any mixture of these. The constituent phase may contain only one type of filler component material or several types of component materials. The filler component may or may not have medical function or other effects to facilitate tissue healing and/or regeneration.

Several prior art patents describe, that oriented bioabsorbable materials and implants (devices) containing powder-like ceramic materials (filler component) can be manufactured by solid state deformation (like drawing) of bioabsorbable (biodegradable) polymers containing particles of a ceramic material, like calciumphosphate, hydroxyapatite, fluoroapatite or tricalciumphosphate, see e.g. U.S. Pat. Nos. 4,898,186, 4,968,317 and 6,228,111 B1. However, prior art does not teach that the filler component could be used to control and change the speed and degree of the change of the shape of a biodegradable polymer composite material or device.

The filler component preferably does not form essential chemical bonds with surrounding polymer matrix material. Thus between the polymer matrix and filler component there are preferably no strong interfacial primary bonds such as covalent or ionic bonds. When the filler and matrix component of the composite material are separate from each other, small cavities and/or voids are typically formed into the polymer matrix around filler component, during the further orientation programming process (solid state deformation). Thus the composite material or device may have a structure which consists within polymer matrix a filler component and preferably small cavities around the filler component. In addition to the cavities, different orientation ratio may be formed in the vicinity of the filler component, such as filler particles, comparing to that of in the polymeric regions lacking the particles. Small cavities may be beneficial in increasing a water absorption, which may further enhance a shape transformation rate of the composite material or device. A shape transformation rate is designated herein as a speed and/or a degree of a change of a shape of a composite material or device.

Filler component may have different shapes such as 1) irregular, ellipsoidal, polyhedral, or spherical particle, with no long dimensions, 2) fibre, with one long dimension, and 3) platelet or lamina, with two long dimensions. Filler component may be also preferably at least partially rigid so that component is at least not in high extent deformed during manufacturing. Partially rigid component may interfere the composite orientation programming process (solid state deformation) and generate an heterogeneously oriented polymer matrix, where the polymer chains may have additional orientation in the vicinity of the filler component. Heterogeneously oriented structure may lead to an enhanced shape transformation rate of a composite material or a device.

Filler component dimensions such as particle size and particle size distribution can be varied to tailor the composite structure and thus adjust the effect of filler component to shape-memory properties. Particle size and particle size distribution may affect on the size of the voids and/or cavities around the fillers particles as well as the orientation heterogeneity around the particles and thus either increase or decrease the degree of shape transformation and/or shape transformation speed towards the evolved shape.

Filler component may have a hydrophilic nature. When the hydrophilic component is used as a filler material the water absorption of a composite or a device may be increased. Increased water uptake may further plasticize the polymeric structure of the composite and further enable deorientation of the polymer structure in physiological conditions. Deorientation means in this context relaxation of the oriented polymer chains. When the deorientation occurs polymer chains at least partially contract towards the non-orientated state. At the beginning of the deorientation there is no or at least no essential degradation of the molecular chains (chain scission). Thus devices and composites which have at least partially hydrophilic nature may have enhanced shape transformation rate.

The composite material or device may also contain one or more biologically active molecules or additives, such as chemotherapeutic agent, anti-inflammatory agent, antibiotic or other drugs, growth factors, anticoagulants etc. Such composite material or device are advantageous in clinical use, because they will further facilitate tissue healing and/or tissue generation or regeneration. These active molecules or additives may or may not enhance the shape transformation rate.

A composite material or device may be manufactured using blending and conventional melt processing techniques like extrusion, injection moulding, compression moulding etc, to form a non-programmed original shape. After conventional melt processing a composite material or device can be further processed (programmed), for example by means of solid state deformation process (orientation programming). This deformation process creates the mechanically active shape-memory capability and properties like maximum shape transformation capability and force the material is able to produce in tissue conditions of the composite or device. Deformation process is designated as programming or orientation programming. A shape of the composite material or device which is formed during programming is designated as a programmed or an initial shape.

In the deformation process, the composite material or device of the original shape is loaded with predetermined tension. The level of the predetermined tension may depend e.g. on the initial geometry of the sample, programming/deformation temperature, deformation speed, cooling speed and deformation ratio. The deformation ratio may also affect the degree of dimensional change and stress generation and relaxation of the composite material or medical device.

The composite material or medical device may be manufactured and programmed so that it has the controlled and predetermined speed to change towards the evolved shape after activation in the physiological conditions. When the polymeric phase of the composite material or device is deformed or programmed through solid state deformation processes, such as die-drawing, oriented polymer chain structure is created (programmed, initial shape). When the programming is done at temperature above polymer's glass transition temperature ($T_g$) but below the melting temperature ($T_m$), if any, of the polymer and quickly cooled to a temperature below $T_g$, the deformed shape, also called programmed or initial shape, becomes frozen or fixed. This initial shape is thus adapted and may have an ability to change towards the evolved shape.

When the external stimulus for shape transformation is given by physiological conditions or conditions simulating the physiological conditions there may occur relaxation/deorientation of the oriented and stressed polymer chains of the initial shape. Physiological conditions means aqueous environment and temperature at the range 35° C. to 42° C. Thus after activation polymer chains tend to contract towards the non-oriented (non-programmed) state, evolved shape, which ultimately is the shape before programming. Although the composite material or device is programmed to change towards the evolved shape it does not necessarily reach the evolved shape nor the original non-programmed shape.

The shape transformation of the composite device may be determined by measuring the dimensions, such as a diameter and length, of the device of initial shape and changed shape. Dimensions of the changed shape may be measured as a function of time.

The degree and/or speed of the dimensional change and thus shape transformation rate of a composite material or device may be predetermined in more controlled way by changing the polymer matrix composition and preferably changing the composition of a composite material by adding an particular amount of filler component. Thus the filler component may be adapted to accelerate and/or amplify and thus to control the degree and/or speed of the shape transformation of the composite material or device. According to the invention, an addition of a filler component may generate more rapid and increased degree of shape transformation which is advantageous for example for initial and short term self-locking and fixation strength of medical devices made of these composite materials. In this context initial means substantially immediate and occurring within a time period of hours and short term designates time period from days to months. The amount of filler component is at maximum 50 weight-% or more and at minimum 0.5 weight-%. However, as the person skilled in the art understands, there should be enough polymer matrix, which could form an oriented polymeric structure. The potential shape transformation (at maximum) of the composite material or device, which takes place during the change from initial shape towards the evolved shape depends on the orientation programming of the composite material. Some examples are given in table below.

TABLE 1

Potential shape transformation.

| Non-programmed rod (diameter D2, mm) | Draw-ratio | Orientation programmed rod (diameter D1, mm) | Potential shape transformation (%) (D2 − D1)/D1 * 100% |
|---|---|---|---|
| 16 | 10 | 5.1 | 216.2 |
| 16 | 8 | 5.7 | 182.8 |
| 16 | 6 | 6.5 | 145 |
| 16 | 4 | 8 | 100 |
| 16 | 2 | 11.3 | 41.4 |
| 6 | 10 | 1.9 | 216.2 |
| 6 | 8 | 2.1 | 182.8 |
| 6 | 6 | 2.5 | 145 |
| 6 | 4 | 3 | 100 |
| 6 | 2 | 4.2 | 41.4 |

The mechanically active shape-memory effect and shape transformation of a composite or device may be based on the deorientation of the oriented, extra oriented (more extended polymer chains in the vicinity of the filler component, such as particles) and stressed polymer chains. However the mechanically active shape-memory potential may also be dependent on the molecular structure, molecular weight and morphology of the polymer such as amorphous, crystalline or semicrystalline structure.

During orientation programming (solid state deformation process) of a composite material or device at least partially additional oriented structure may be formed. This additional oriented structure means in this context that at least some of the polymer chains, which are oriented during the process, are more oriented (more extended) and have higher orientation ratio than the rest of the polymer chains. This may be due to the filler component like particles which interfere with the deforming process.

EXAMPLE 1

P(L/D)LA 50L/50D and β-TCP are melt mixed in twin screw extruder and extruded into round rods having the diameter of 3 mm. The extruder temperatures are between 50° C. and 280° C. The 3 mm rods are then die drawn into 1.5 mm rods with drawing temperatures between 60° C. and 120° C. and subsequently cooled down to room temperature. The draw ratio of the programmed rods is then 4. Similar rods are made of pure P(L/D)LA 50L/50D. Internal structures of these materials are presented in FIG. 3 and FIG. 4. In simulated body conditions, in vitro, the programmed P(L/D)LA 50L/50D-βTCP-composites have remarkably shorter latency time before the shape transformation starts, higher short term shape transformation and higher shape transformation speed than the pure P(L/D)LA 50L/50D copolymer processed similar way, as presented in FIGS. 5 A and 5 B.

EXAMPLE 2

PLGA 85L/15G and β-TCP are melt mixed in twin screw extruder and extruded into round rods having the diameter of 5.5 mm. The extruder temperatures are between 50° C. and 300° C. The 5.5 mm rods are then die drawn into 2.7 mm grooved surfaced rods with drawing temperatures between 60° C. and 140° C. and subsequently cooled down to room temperature. The draw ratio of the programmed rods is then 4.1. In simulated body conditions, in vitro, the programmed PLGA 85L/15G-βTCP-composites have remarkably shorter latency time before the shape transformation starts, higher short term shape transformation and shape transformation speed than the pure PLGA 85L/15G copolymer, as presented in FIG. 6. Shape transformation ratio is according to the β-TCP concentration (0, 10, 15 and 20 wt-%) of the composite; the higher particle concentration the higher shape transformation ratio in the simulated body conditions.

FIG. 1. shows a schematic figure of a shape transformation and a change of a shape of a composite material or device when it has a shape-memory capability. As presented in FIG. 1. the composite material or device of present invention have an ability to change from programmed initial shape 1 towards the evolved shape 2. The dimensions are presented as length L1 and diameter D1 for the programmed initial shape and length L2 and diameter D2 for evolved shape. The composite material or medical device has a programmed initial shape and at least one evolved shape. The initial programmed shape is adapted to change towards the evolved shape when the composite material or medical device is activated in physiological conditions or in conditions simulating the physiological conditions. The degree and/or speed of the shape transformation of the composite material or device may be adjusted by controlling the amount and type of the filler component.

Figure 2:
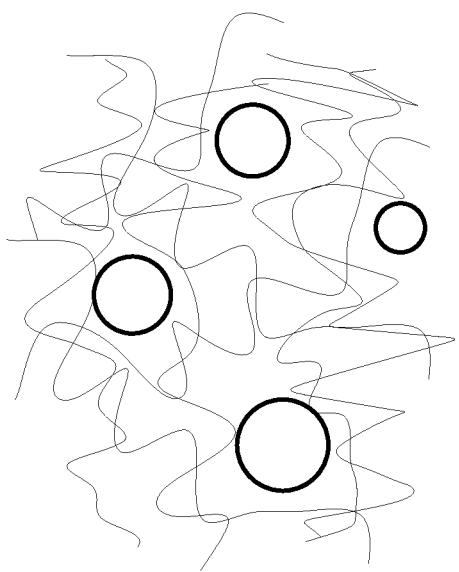
FIG. 2 shows a schematic figure of an internal structure of a composite material or device after conventional melt processing having a non-oriented (non-programmed), original structure (2 A) and after solid state deformation process having an orientation programmed, initial structure (2 B)
Figure 2:
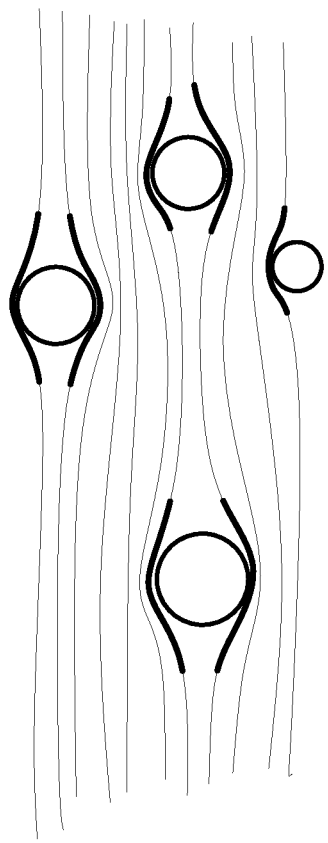

FIG. 2. shows a principle internal view of a composite material or device after conventional melt processing having a non-oriented, original structure (2 A) and after orientation programming process (solid state deformation) having an oriented (programmed), initial structure (2 B). Partially rigid components (like spheres in a figure) may interfere the composite solid state deformation process and generate an heterogeneously oriented polymer matrix, where the polymer chains may have additional orientation and higher orientation rate in the vicinity of the filler component (shown by darker line around the spheres). Heterogeneous orientation may further have influence on the transformation rate profile of the composite material or device.

Figure 3:
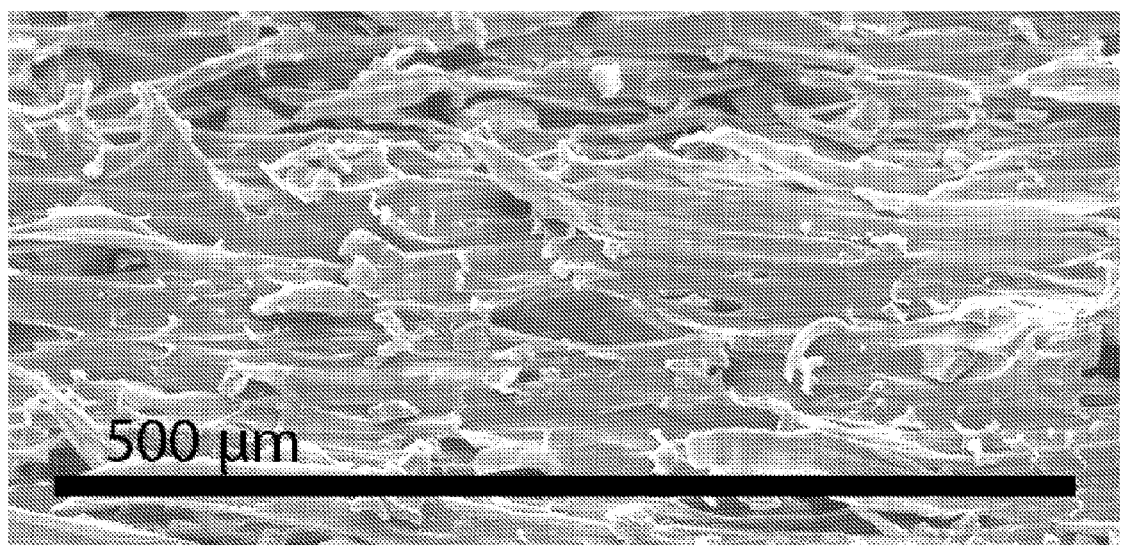
FIG. 3 is a scanning electron microscope (SEM) figure of an internal structure of an orientation programmed composite P(L/D)LA 50L/50D/β-TCP (10 wt-%) according to an example embodiment of the present invention.
Figure 4:
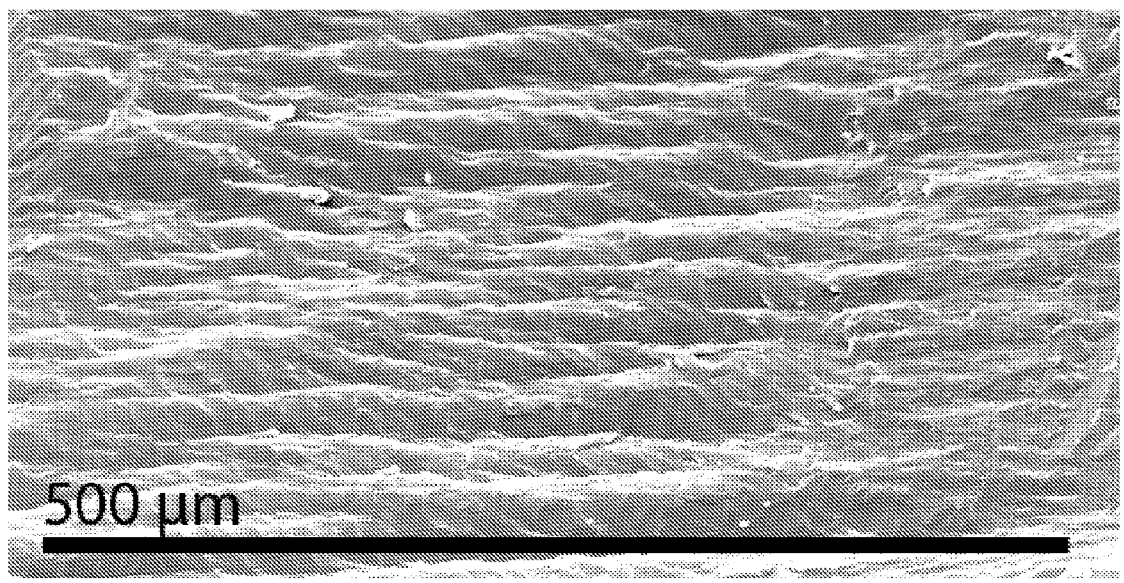
FIG. 4 is a SEM figure of an internal structure of an orientation programmed P(L/D)LA 50L/50D.

According to an example embodiment of the present invention an initial internal structure of an orientation programmed composite, P(L/D)LA 50L/50D/β-TCP (10 wt-%), with draw ratio 4 is shown in FIG. 3. Internal structure of an orientation programmed polymer, P(L/D)LA 50L/50D with draw ratio 4, is shown in FIG. 4.

Figure 5:
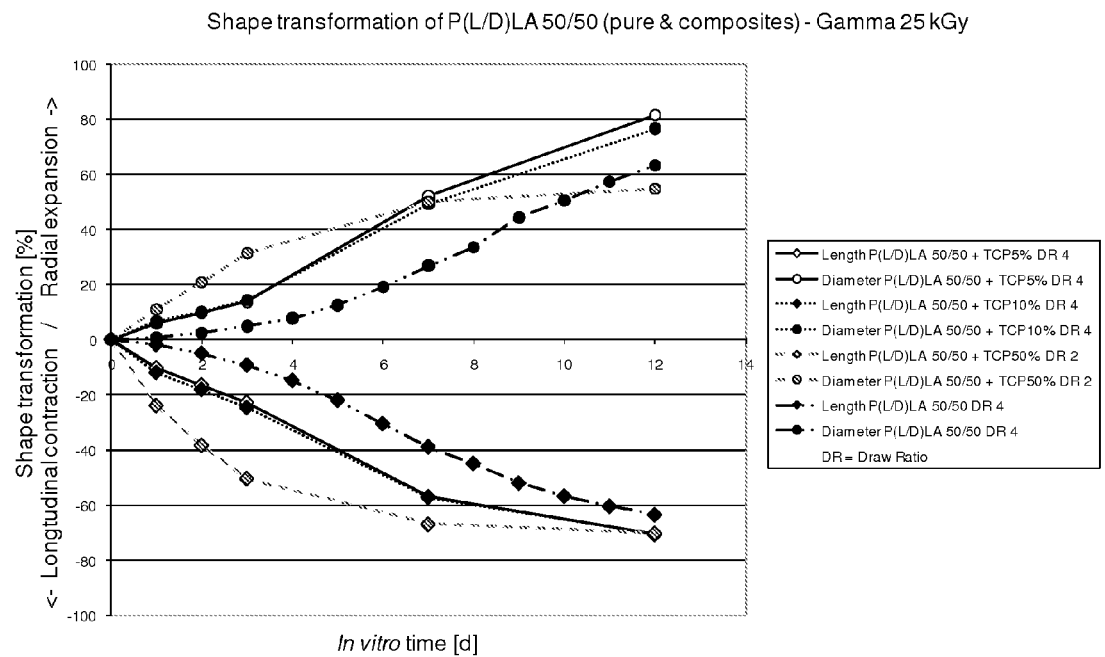
FIG. 5A-B shows diagrams on the shape transformation of a pure copolymer (P(L/D)LA 50L/50D) and composites of P(L/DL)LA 50/50 with β-tricalciumphosphate in simulating physiological conditions (in vitro)
Figure 5:
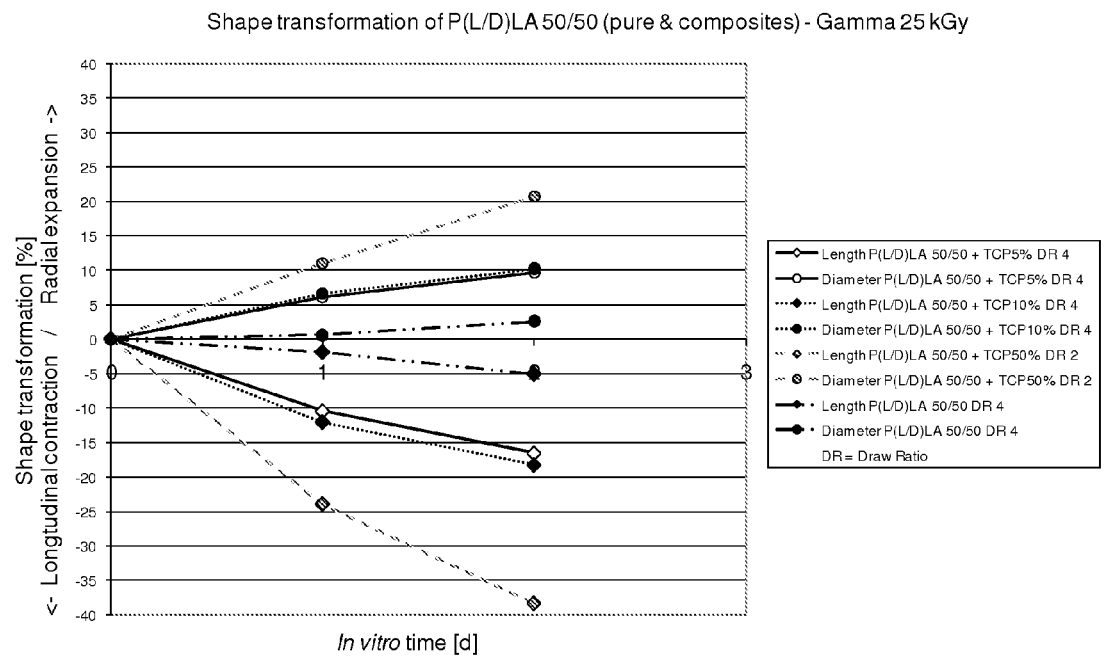

FIG. 5. A and B present the acceleration and amplification of the shape transformation rate in a well controlled manner by adding filler particles. The tests were carried out by immersing the samples in phosphate buffered saline at 37° C. and periodically measuring the dimensions manually using a slide gauge. In vitro time (days) is presented in x-axis and shape transformation (%) in y-axis. Radial expansion (change in diameter upwards) and longitudinal contraction (change in length downwards) of y-axis. The dimensional change which takes place during the shape transformation in physiological conditions, may be remarkably increased when the material is blended with particle filler material. For example the diameter of the composites which has 10 weight-% filler may be increased by 10% in 2 days, whereas the length may be decreased by 18%, as presented in FIG. 5 B. Pure copolymer P(L/D)LA 50L/50D has less shape transformation capability and normally 24 to 48 h time lag of shape transformation to occur at the beginning of exposure to physiological conditions. It is obvious that filler component and thus particle blending change the transformation rate profile of composites. The time lag diminishes and shape transformation rate can be adjusted to desired and predetermined level by varying the particle content. Increased shape transformation may be achieved also with relatively small particle content e.g. such as from 5 to 10 weight-%.

Figure 6:
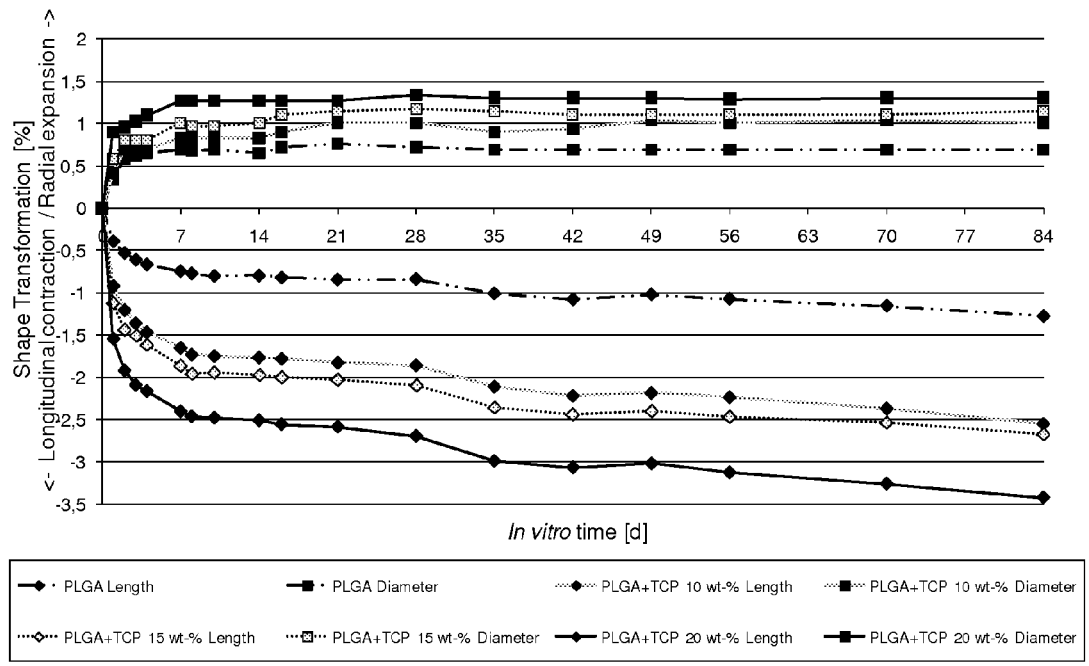
FIG. 6 shows a diagram on the shape transformation of pure copolymer PLGA 85/15 and composites of PLGA 85/15 with β-tricalciumphosphate in simulating physiological conditions (in vitro)

FIG. 6. shows a diagram of a shape transformation of a pure copolymer PLGA 85L/15G and composites of PLGA 85L/15G with β-tricalciumphosphate in physiological conditions until 84 days. The test is carried out by immersing the samples in phosphate buffered saline at 37° C. and periodically measuring the dimensions manually using a slide gauge. In vitro time (days) is presented in x-axis and shape transformation (%) in y-axis. Radial expansion (change in diameter upwards) and longitudinal contraction (change in length downwards) of y-axis. The dimensional change, both diameter and length, is rapid at the beginning of the hydrolysis. For example by 7 days all the materials have reached most of the transformation of the sample length, which thereafter continues slow decrease until 84 days. The shape transformation rate of the composite materials or devices may thus be enhanced at the beginning of the immersion.

Figure 7:
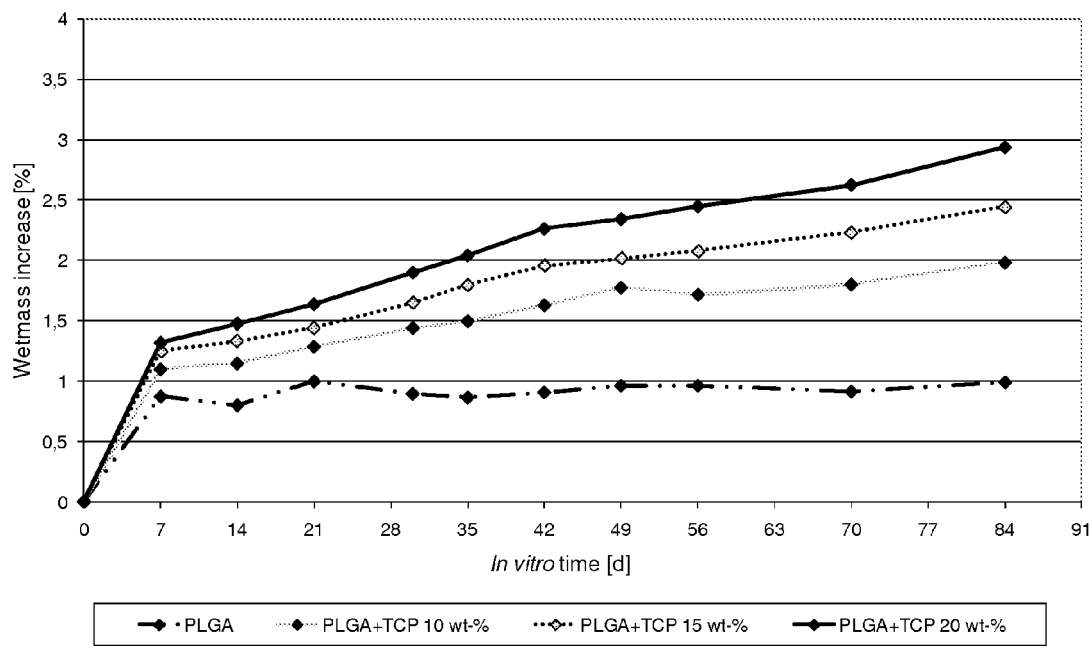
FIG. 7 shows a diagram on the weight change of pure copolymer PLGA 85/15 and composites of PLGA 85/15 with β-tricalciumphosphate in simulating physiological conditions, in vitro, due to the water absorption.

FIG. 7. shows a diagram on the weight change of pure copolymer PLGA 85L/15G and composites of PLGA 85L/15G with β-tricalciumphosphate particles in physiological conditions due to the water absorption. The test is carried out by immersing the samples in phosphate buffered saline at 37° C. and periodically weighing the samples. In vitro time (days) are presented in x-axis and wet mass increase (%) in y-axis. As seen the hydrophilic filler particles increase the wet mass of the composites during the whole period, 84 days. Wet mass of a pure polymer is increased from 0.8 to 1.2 weight-% during 84 day follow up time whereas the wet mass of composite having 20 weight-% particles is increased from 1.3 to 3.6 weight-%. Thus water absorption of composite materials or devices may be increased by adding a hydrophilic filler component into the polymer matrix.

The embodiments described above are only exemplary embodiments of the invention and a person skilled in the art recognizes readily that they may be combined in various ways to generate further embodiments without deviating from the basic underlying invention.

The invention claimed is:

1. A biodegradable composite material or device having an orientation programmed initial shape having orientation draw ratio between 2 and 10, and at least one evolved shape being different from the initial shape, wherein the orientation programmed initial shape adapts toward a predetermined tension level and is capable of restoring the predetermined tension level by stress generation or relaxation, and wherein the material or device comprises:

a biodegradable polymer matrix material consisting of L-lactide/D-lactide copolymer or L-lactide/glycolide copolymer and a filler component consisting of β-tricalciumphosphate in an amount between 5 and 15 weight -%, and wherein the composite material or device has a structure consisting of polymer matrix having a uniaxial heterogeneous orientation and cavities around filler component particles, wherein the structure accelerates or amplifies transformation from the initial shape towards the evolved shape when an external stimulus for transformation is given by physiological conditions comprising an aqueous environment and a temperature of 35° C. to 42° C. thus enabling a shortened latency time of the transformation or amplified transformation of dimensions of the material or device as compared to a material or device without the filler component.

2. The composite material or device according to claim 1, wherein the filler component does not form essential bonds with surrounding biodegradable polymer matrix material.

3. The composite or device according to claim 1, wherein said filler component has buffering property.

4. The composite material or device according to claim 1, wherein said filler component enhances visibility.

* * * * *